United States Patent [19]

Murad et al.

[11] Patent Number: 5,328,913
[45] Date of Patent: Jul. 12, 1994

[54] MINOXIDIL ANALOGS AS INHIBITORS OF CELL PROLIFERATION AND LYSYL HYDROXYLASE

[75] Inventors: Saood Murad; Sheldon R. Pinnell, both of Durham, N.C.

[73] Assignee: Duke University, Durham, N.C.

[21] Appl. No.: 987,952

[22] Filed: Dec. 11, 1992

[51] Int. Cl.⁵ .......................................... A61K 31/505
[52] U.S. Cl. ..................................... 514/275; 514/256
[58] Field of Search ...................... 514/256, 272, 275; 544/300, 323

[56] References Cited

U.S. PATENT DOCUMENTS

| | | | |
|---|---|---|---|
| 3,998,827 | 12/1976 | Thomas, Jr. et al. | 544/323 |
| 4,912,111 | 3/1990 | Sank et al. | 514/256 |
| 5,002,949 | 3/1991 | Peseckis et al. | 514/256 |
| 5,114,943 | 5/1992 | Ulrich | 514/256 |

OTHER PUBLICATIONS

Priestley et al., "The metabolism of fibroblasts from normal and fibrotic skin is inhibited by minoxidil in vitro", British Journal of Dermatology (1991) 125:217-221.

Hautala et al., "Minoxidil specifically decreases the expression of lysine hydroxylase in cultured human skin fibroblasts", Biochem. J. (1992) 283:51-54.

Hughes et al., "Minoxidil-Induced Changes in the Contraction of Collagen Lattices by Human Skin Fibroblasts", Plastic and Reconstructive Surgery, Apr. 1992, vol. 89, No. 4, pp. 722-730.

Murad et al., "Suppression of Fibroblast Proliferation and Lysyl Hydroxylase Activity by Minoxidil", Journal of Biological Chemistry, American Society for Biochemistry and Molecular Biology, Inc., vol. 262, No. 25, Issue of Sep. 5, 1987, pp. 11973-11978.

Murad et al., "Structure-Activity Relationship of Minoxidil Analogs as Inhibitors of Lysyl Hydroxylase in Cultured Fibroblasts", Archives of Biochemistry and Biophysics, vol. 292, No. 1, Jan. 1992, pp. 214-238.

Murad et al., "Structure-Function Relationship for Suppression of Skin Fibroblast Lysyl Hydroxylase Activity by Minoxidil", J. Invest. Dermatol. vol. 90, No. 4 Apr. 1988.

*Primary Examiner*—Frederick E. Waddell
*Assistant Examiner*—T. J. Criares
*Attorney, Agent, or Firm*—Nixon & Vanderhye

[57] ABSTRACT

The present invention relates to a method of inhibiting cell proliferation and lysyl hydroxylase expression. The method involves the use of minoxidil derivatives. The inhibitory activity of hydroxy derivatives of minoxidil is such that these compounds can be used as selective antifibrotic agents.

13 Claims, 8 Drawing Sheets

MINOXIDIL ANALOGS AS INHIBITORS OF CELL PROLIFERATION AND LYSYL HYDROXYLASE

This invention was made with government support under Grant No. R01-AR-17128-15 awarded by the National Institutes of Health. The government has certain rights in this invention.

TECHNICAL FIELD

The present invention relates to a method of inhibiting cell proliferation and lysyl hydroxylase activity that involves the use of minoxidil analogs.

BACKGROUND

Although the underlying mechanism leading to tissue fibrosis is not entirely clear, the hallmark of a fibrotic response is the excessive accumulation of collagen resulting from enhanced fibroblast proliferation and collagen production. The most specific way to interfere with collagen overproduction would be at the level of post-translational modifications unique to collagen biosynthesis. Two such modifications that have received considerable attention as potential sites for pharmacological intervention are the intracellular hydroxylation of susceptible proline residues, catalyzed by prolyl hydroxylase, and the extracellular oxidation of selected lysine residues, catalyzed by lysyl oxidase.

The present invention provides a novel pharmacological approach to interfere with collagen biosynthesis involving lysyl hydroxylase as the target enzyme. Catalyzing the synthesis of hydroxylysine during collagen biosynthesis, this post-translational modifying enzyme is critically important in the formation of intermolecular crosslinks that stabilize the fibrillar structure of collagen. Its activity is increased during lung fibrosis, leading to enrichment of hydroxylysyl crosslinks in newly synthesized collagen. Inhibition of lysyl hydroxylase would result in the synthesis of a collagen deficient in hydroxylysine, and, therefore, hydroxylysine-derived crosslinks. Such a collagen would be deposited in the extracellular matrix as a non-functional protein and would also be more susceptible to degradation by collagenase, limiting its amount in the fibrotic tissue.

Inhibition of crosslinking at the level of lysyl hydroxylation has a distinct advantage in that it would lead to inhibition of collagen biosynthesis without affecting the biosynthesis of elastin which lacks hydroxylysine, thus avoiding cardiovascular side-effects seen with crosslink inhibitors that act at the level of lysyl oxidation or subsequent condensation.

Minoxidil has been identified as a pharmacological agent that has the unique ability to selectively decreased the activity of lysyl hydroxylase in cultured fibroblasts, apparently by inhibiting enzyme synthesis at the transcriptional level. (See Murad and Pinnell, J. Biol. Chem. 262:11,973 (1987), see also generally Hautala et al, Biochem. J. 283:51 (1992)). In addition, minoxidil is capable of inhibiting the serum-induced proliferation of fibroblasts in culture, a property that would serve to further reduce the amount of collagen in the fibrotic tissue. However, the hypotensive activity of minoxidil is a deterrent in its use as an antifibrotic drug in normotensive patients.

Figure 1:
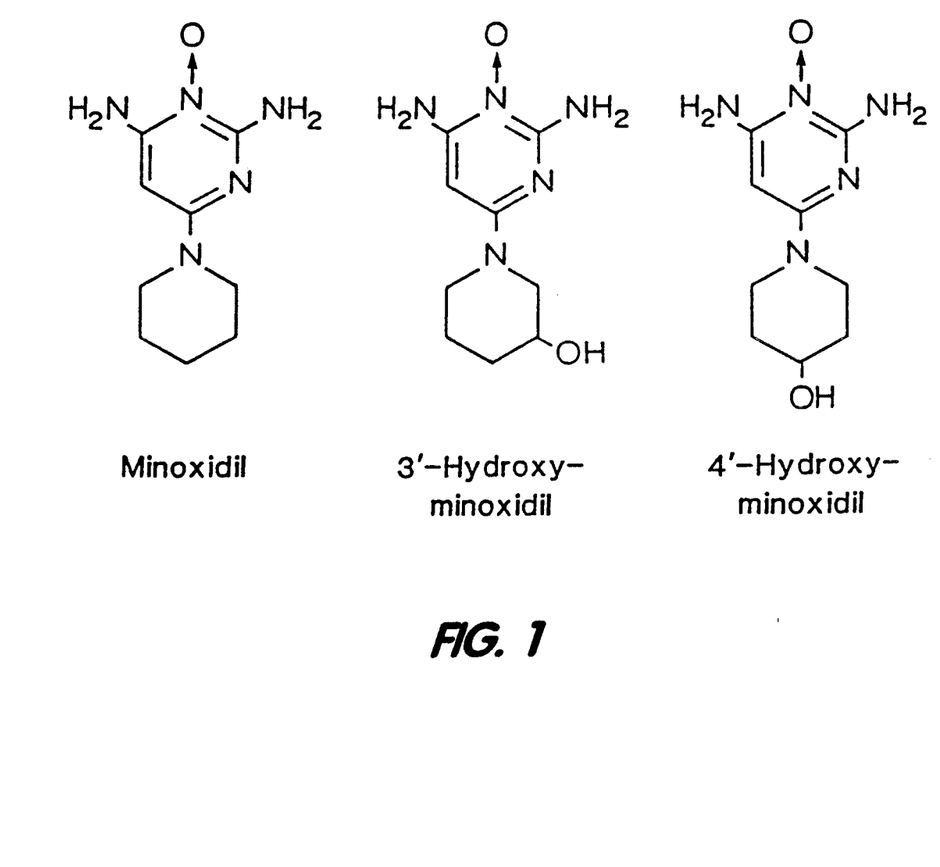
FIG. 1 shows the structures of minoxidil, 3'-hydroxyminoxidil and 4'-hydroxyminoxidil.

The present invention results, at least in part, from the discovery that two derivatives of minoxidil, 3'-hydroxyminoxidil and 4'-hydroxyminoxidil (see FIG. 1; see also U.S. Pat. No. 3,998,827), are inactive as antihypertensive agents, but are as active as minoxidil in suppressing fibroblast proliferation and lysyl hydroxylase activity. The hydroxy derivatives of minoxidil are also more water soluble than the parent compound, are not cytotoxic even at a high concentration (5 mM), and retain the enzyme suppressing activity at this concentration, at which minoxidil mysteriously loses its effect. The hydroxyminoxidils are thus preferred candidates for antifibrotic drugs.

OBJECTS AND SUMMARY OF THE INVENTION

It is a general object of the invention to provide a method of inhibiting tissue fibrosis.

It is a specific object of the invention to provide a method of selectively inhibiting lysyl hydroxylase.

Further objects and advantages of the invention will be clear to one skilled in the art from a reading of the description that follows.

The present invention relates to a method of selectively interfering with a fibrotic response by reducing collagen overproduction. The selectively of the method is such that biosynthesis of elastin would not be compromised and cardiovascular side effects would be avoids.

DETAILED DESCRIPTION OF THE INVENTION

The present invention relates to a method of inhibiting lysyl hydroxylase. The method comprises contacting collagen-biosynthesizing cells with a minoxidil derivative under conditions such that the hydroxylase activity is reduced. Advantageously, the minoxidil analog used is a hydroxy derivative, eg., 3'-hydroxyminoxidil or 4'-hydroxyminoxidil (see U.S. Pat. No. 3,998,827 (Upjohn)). These two derivatives, which have an inhibitory potential comparable to that of minoxidil, exert a selective effect in that they inhibit the expression of lysyl hydroxylase without affecting prolyl hydroxylase.

Lysyl hydroxylase is a critical enzyme in collagen biosynthesis. Thus the ability to inhibit expression of the enzyme offers a clinical means of limiting collagen accumulation in fibrotic conditions. The hydroxy derivatives of minoxidil are preferred agents for such use as they lack the hypotensive activity of minoxidil itself. In addition, the water solubility of these compounds is greater than that of minoxidil. The hydroxy derivatives of minoxidil are thus advantageous over the parent compound as a potential antifibrotic agent.

The minoxidil derivatives of the invention can be formulated as a pharmaceutical composition suitable for oral use, for example, as a tablet, capsule, solution, suspension or emulsion; for topical use, for example, as a cream, ointment, gel or lotion; or for parenteral use, for example, as a sterile solution or suspension. The composition may take other forms, for example, a suppository or ophthalmic formulation suitable for topical application to the eye.

The composition can be prepared in a conventional manner using conventional pharmaceutically acceptable carriers in solid or liquid dosage form. The hydroxyminoxidil derivative can be present in the composition as the sole active agent or it can be present in combination with other drugs.

The amount of active ingredient to be administered depends on the patient (or animal, in the case of veterinary use) (eg. weight and age) and on the specific nature of the condition and the treatment protocol to be used. An appropriate dose range can be readily determined but can be expected to be about 0.5 to about 30 mg per kg of body weight, preferably, about 1 to about 2 mg per kg of body weight. The dose range for a patient can be expected to range from about 35 to about 2000 mg per day, administered either as a single dose or as a multiple divided dose. Preferably the dose for a patient is about 70 to about 140 mg per day. Veterinary doses will be proportional to patient doses, with appropriate adjustment made to take into account weight differences.

A detailed description of appropriate pharmaceutical compositions can be found in U.S. Pat. No. 3,998,827.

The minoxidil derivatives of the invention can be used in clinical settings where interruption of the process of collagen deposition is desirable. The derivatives can thus be used in the treatment of fibrotic conditions including scleroderma, cirrhosis, pulmonary fibrosis, keloids, myelofibrosis, nephrosclerosis, radiation fibrosis, and drug fibrosis. The derivatives can also be used to manage abnormal wound healing such as in hypertrophic scar formation. The derivatives can also be used to control post surgical scarring that occurs, for example, after glaucoma filtration surgery and cross-eye surgery. Post surgical adhesions can also be treated with the derivatives of the invention, as can fibromatous disorders. It is contemplated that control of excessive collagen crosslink formation during the aging process can also be effected using the hydroxyminoxidil derivatives. These derivatives can also serve as useful agents for the treatment of conditions such as proliferative vitreoretinopathy and bleb scarring after trabeculectomy, disorders associated with unwanted cell proliferation and collagen production.

Certain aspects of the present invention are described in greater detail in the non-limiting Examples that follow. (See also Murad et al, Arch. Biochem. Biophys. 292:234 (1992)). In addition, the date presented below demonstrate that the hydroxy derivatives of minoxidil are not cytotoxic to non-proliferating fibroblasts even at a concentration of 5 mM:

| Treatment (72 hr) | $10^{-6}$ × No. of Cells/Dish |
| --- | --- |
| Control | 1.44 |
| Minoxidil (5 mM) | 0.49 |
| 3'-Hydroxyminoxidil (5 mM) | 1.39 |
| 4'-Hydroxyminoxidil (5 mM) | 1.42. |

Further, the following data demonstrate that, unlike minoxidil, the hydroxy derivatives retain lysyl hydroxylase suppressing activity at 5 mM:

| Treatment (48 hr) | Fibroblast Lysyl Hydroxylase Activity (cpm$^3$H$_2$O/mg protein) |
| --- | --- |
| Control | 1589 |
| Minoxidil (1 mM) | 378 |
| Minoxidil (5 mM) | 1321 |
| 3'-Hydroxyminoxidil (1 mM) | 401 |
| 3'-Hydroxyminoxidil (5 mM) | 383 |
| 4'-Hydroxyminoxidil (1 mM) | 415 |
| 4'-Hydroxyminoxidil (5 mM) | 494. |

The data set forth below show the selective effect of minoxidil and its hydroxy derivatives (1 mM) on lysyl hydroxylase (cpm$^3$H$_2$O/mg protein) and lysyl hydroxylation in human skin fibroblasts:

| Treatment (72 hr) | Prolyl Hydroxylase Activity | Lysyl Hydroxylase Activity |
| --- | --- | --- |
| Control | 26762 | 1211 |
| Minoxidil | 29446 | 308 |
| 3'-Hydroxyminoxidil | 30512 | 263 |
| 4'-Hydroxyminoxidil | 33500 | 293 |
|  | Hyp/Pro[a] | Hyl/Lys[a] |
| Control | 0.92 ± 0.00 | 0.22 ± 0.03 |
| Minoxidil | 0.92 ± 0.01 | 0.07 ± 0.02 |
| 3'-Hydroxyminoxidil | 0.95 ± 0.02 | 0.07 ± 0.01 |
| 4'-Hydroxyminoxidil | 1.12 ± 0.07 | 0.09 ± 0.01 |

[a]Mean ± range of values from two separate experiments; the values are for type I procollagen chains isolated by gel electrophoresis.

EXAMPLE 1

Effect of Minoxidil, Minoxidil Sulfate, Deoxyminoxidil, and Hydroxyminoxidils on Lysyl Hydroxylase Activity Minoxidil and its structural analogs were a gift from the Biological Screening Office, The Upjohn Company, Kalamazoo, Mich. 2-Hydroxypyridine-N-oxide, 3-hydroxypyridine-N-oxide, and 4-phenylpyridine-N-oxide were obtained from Aldrich Chemical Company, Milwaukee, Wis. All other N oxides were bought from Sigma Chemical Company, St. Louis, Mo.

Skin fibroblast cultures derived from an apparently normal 14-month-old boy (GM05659) were obtained from the Institute for Medical Research, Camden, N.J. The cells were subcultured by trypsinization and used before 25 population doublings. Typically, $4 \times 10^5$ cells were seeded onto 100-mm (diameter) plastic petri dishes and allowed to grow in 10 ml of Dulbecco's modified Eagle's minimum essential medium containing 5.6 mM glucose, buffered in pH 7.4 with 24 mM sodium biocarbonate/25 mM Hepes and supplemented with 20% (v/v) calf serum which had been inactivated for 30 min at 56° C. The cells were incubated at 37° C. in a humidified atmosphere of 5% $CO_2$ plus 95% air.

After a week, the medium was replaced with medium supplemented with 0.5% heat-inactivated diaylzed calf serum, and the incubation was continued for 72 h in the presence of minoxidil or one of its structural analogs. The compounds were dissolved in 95% ethanol, except minoxidil sulfate which was dissolved in acetone; the final solvent concentration was 1% (v/v). During the last 3 h of incubation, cells received 100 $\mu$M Na L-ascorbate to ensure complete hydroxylation of the polypeptide precursors of precollagen (Murad et al, J. Invest. Dermatol. 75:404 (1980)).

The medium was then removed and the cells were washed twice with a solution containing 0.14 M NaCl, 5 mM KCl, 0.3 mM $Na_2PO_4$, and 0.4 mM $KH_2PO_4$, adjusted to pH 7.4. The cells were detached from the plates with a solution containing 0.05% trypsin, 0.54 mM EDTA, 5.5mM glucose, 6.90mM $NaHCO_3$, 0.14 mM NaCl, and 5 mM KCl. The trypsinization was terminated with 2 vol of 20% serum-supplemented medium, and the cell number in an aliquot of the suspension was determined using a Coulter counter.

The detached cells were collected by centrifugation at 500g for 6 min at 4° C. washed twice by suspending in phosphate-buffered NaCl/KCl as above, and then centrifuged. The cell pellet was suspended in a medium (1 ml/$5 \times 10^6$ cells) containing 0.2 M NaCl, 0.1 M glycine, 50 $\mu$M dithiothreitol, 20 mM Tris-HCl, buffer (pH 7.5), 0.1% Triton X-100, and 0.01% soybean trypsin inhibitor. The suspension was sonicated for 30 s using a Branson sonifier cell disrupter. The lysate was centrifuged at 27,000g for 1 h at 4° C., and the resulting supernatant was used for prolyl and lysyl hydroxylase assays (Murad and Pinnell, J. Biol. Chem. 262:11, 973 (1987)). The enzyme activities are based on a unit of soluble cell protein.

The protein content of cell extracts was determined by a dye-binding technique using Bio-Rad reagent and protein standard (Bradford, Anal. Biochem. 72:248 (1976)).

The lysyl hydroxylase inhibitory potential of minoxidil and certain nitroxides is summarized in Table I.

TABLE I

Effect of Some Organic Nitroxides on Lysyl Hydroxylase Activity in Cultured Fibroblasts

| Compound | Lysyl hydroxylase activity (%) |
|---|---|
| Minoxidil | 28 |
| 2-Hydroxypyridine-N-oxide[a] | 144 |
| 3-Hydroxypyridine-N-oxide | 99 |
| 5,5-Dimethyl-1-pyrroline-N-oxide | 103 |
| 4-Hydroxy-2,2,6,6-tetramethylpiperidine-N-oxyl | 130[d] |
| 4-Phenylpyridine-N-oxide[a] | 99 |
| Guanine 3-N-oxide[b] | 132 |
| Isonicotinic acid N-oxide[c] | 90 |

Note: Cultures of human skin fibroblasts grown to confluence were incubated for 72 h in medium supplemented with 1% ethanol containing 1 mM of the indicated compounds. Cells were then harvested, and the enzyme activity in extracts of these cells was measured by a tritium-release assay. The data are expressed as percentages of values for solvent-treated controls.
[a]0.3 mM; dissolved in ethanol; final concentration, 0.3%
[b]Dissolved in NaOH; final concentration, 0.001 N.
[c]Dissolved in aqueous medium.
[d]Average of values from two separate experiments that agreed within 3%.

Minoxidil decreased the level of activity by 72%. None of the other nitroxides had an inhibitory effect. 2-Hydroxy-pyridine-N-oxide and the piperidine and guanine N-oxides actually increased the level of activity by 30–40%.

Figure 2:
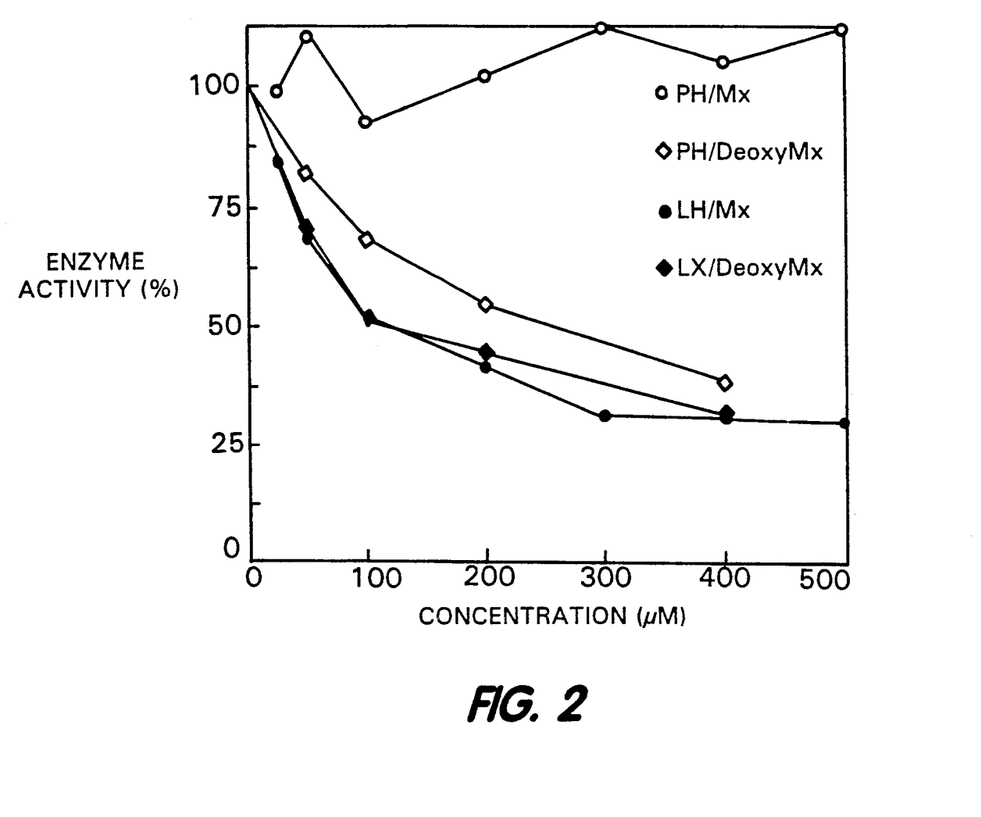
FIG. 2 shows dose response of changes in prolyl and lysyl hydroxylase activities of fibroblasts treated with minoxidil or deoxyminoxidil. Cultures of human skin fibroblasts grown to confluence were incubated for 72 h in medium supplemented with 1% ethanol containing various concentrations of minoxidil or deoxyminoxidil as indicated. Cells were then harvested, and the enzyme activities in extracts of these cells were measured by tritium-release assays (Murad and Pinnell, J. Biol. Chem. 262:11,973 (1987)). The results are expressed as percentages of zero-concentration values.

The functional significance of the nitroxide oxygen in minoxidil was evaluated with a deoxy analog. Shown in FIG. 2 is a comparison of the effects of minoxidil and deoxyminoxidil on the activities of lysyl hydroxylase and the control enzyme prolyl hydroxylase in cultured fibroblasts. At concentrations up to 400 $\mu$M, deoxyminoxidil suppressed lysyl hydroxylase activity in a manner remarkably similar to that observed with minoxidil. The concentration required for 50% inhibition was 118 $\mu$M for both compounds. Unexpectedly, deoxyminoxidil also suppressed prolyl hydroxylase activity in a dose-related manner such that the concentration required for 50% effect was 260 $\mu$M. By contrast, minoxidil over the entire concentration range had no significant effect on prolyl hydroxylase activity. Mixing experiments with extracts of deoxyminoxidil-treated cells and controls provided no evidence for direct inhibition of enzyme activity as a possible mechanism.

Figure 3:
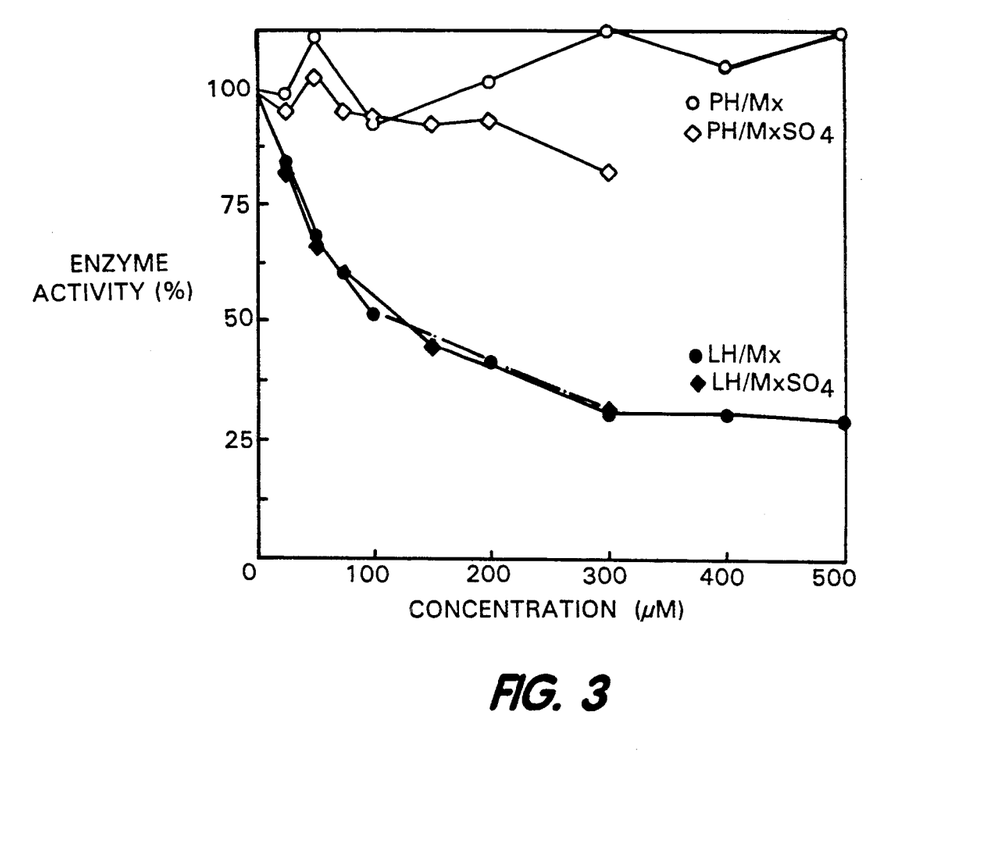
FIG. 3 shows a dose-response of changes in prolyl and lysyl hydroxylase activities of fibroblasts treated with minoxidil or its sulfate. Cultures of human skin fibroblasts grown to confluence were incubated for 72 h in medium supplemented with 1% ethanol containing various concentrations of minoxidil or with 1% acetone containing various concentrations of minoxidil sulfate, as indicated. Cells were then harvested, and the enzyme activities in extracts of these cells were measured by tritium release assays (Murad and Pinnell, J. Biol. Chem. 262:11,973 (1987)). The results are expressed as percentages of zero-concentration values.

A metabolic transformation of minoxidil involves NO-linked sulfation at position 1 of the pyrimidine ring. Minoxidil sulfate is presumed to be the metabolite responsible for the antihypertensive effect of minoxidil (McCall et al, J. Med. Chem. 26:1791 (1983)). The effect of various concentrations of minoxidil sulfate on lysyl hydroxylase activity in cultured fibroblasts is shown in FIG. 3. Because of the limited solubility of minoxidil sulfate when acetone was used as the solvent, concentrations higher than 500 $\mu$M could not be tested. Nevertheless, minoxidil sulfate suppressed lysyl hydroxylase activity in a manner almost identical to that observed with minoxidil. Furthermore, minoxidil sulfate elicited no change in prolyl hydroxylase activity (FIG. 3) and failed to inhibit lysyl hydroxylase activity in vitro, thus essentially reproducing the effect of minoxidil.

Another metabolic transformation of minoxidil involves hydroxylation at position 3 or 4 of the piperidine ring to form 3'-hydroxyminoxidil and 4'-hydroxyminoxidil. Neither metabolite exhibits the marked hypotensive activity associated with minoxidil. In cultured fibroblasts, the hydroxy derivatives (compounds I, II) at equimolar concentration suppressed lysyl hydroxylase activity to an extent practically indistinguishable from that produced by minoxidil (see Table II).

TABLE II

Effect of Minoxidil and Its Structural Analogs on Lysyl Hydroxylase Activity in Cultured Fibroblasts

| Compound | Substituents on pyrimidine ring | Piperidine ring replacement | Lysyl hydroxylase activity (%) |
|---|---|---|---|
| Minoxidil | 2,6-diNH$_2$ | — | 19–39 |
| I | 2,6-diNH$_2$ | 3-Piperidinol | 24 |
| II | 2,6-diNH$_2$ | 4-Piperidinol | 23 |
| III | 2-CH$_3$, 6-NH$_2$ | — | 32 |
| IV | 2-NH$_2$, 6CH$_3$ | — | 37 |
| V | 2,6-diCH$_3$ | | 111 |
| VI | 2-NH$_2$, 5-NO$_2$, 6 CH$_3$ | — | 34 |
| VII | 2-NH$_2$, 6-CH$_3$ | Pyrrolidine | 88 |
| VIII | 2-NH$_2$, 6-CH$_3$ | Morpholine | 91 |
| IX[a] | 2,6-diNH$_2$ | N-Methylpiperazine | 109 |

Note: Cultures of human skin fibroblasts grown to confluence were incubated for 72 h in medium supplemented with 1% ethanol containing 1 nM of the indicated compounds. Cells were then harvested, and the enzyme activity in extracts of these cells was measured by a tritium-release assay. The results are expressed as percentages of values for ethanol-treated controls. The data derived from five separate experiments, each including a minoxidil-treated group. Values for analog-treated groups between experiments did not differ by more than 15%.
[a]0.1 mM; dissolved in HCl; final concentration, 0.0012 N. Under these conditions, minoxidil gave 45% of control activity.

A number of minoxidil analogs containing a modified pyrimidine or piperidine ring were examined for their inhibitory potential toward lysyl hydroxylase in cultured fibroblasts (see Table II). Substitution of the amino group in position 2 or 6 of the pyrimdine ring with a methyl group yielded compounds III and IV which suppressed lysyl hydroxylase activity to levels comparable to those produced by minoxidil. When both amino groups were replaced with methyl groups, the resulting compound V was completely inactive. Introduction of a nitro group in position 5 of the 6-methyl analog, yielding compound VI, had no significant effect on its inhibitory activity. When the piperidine ring was replaced with a pyrrolidine, morpholine, or N-methylpiperazine ring, the resulting compounds VII, VIII, and IX were also inactive.

EXAMPLE 2

Effect of Pyridine, Triazine and N-alkyl Analogs of Minoxidil on Lysyl Hydroxylase Activity

Cell Treatment

Cultures of human skin fibroblast (1.5×10$^6$ cells) were seeded onto 100-mm plates and incubated at 37° in Dulbecco's modified Eagle's medium supplemented with 20% calf serum. After 24 hr, the medium was replaced with medium supplemented with 0.5% heat-inactivated dialyzed calf serum. The incubation was continued for an additional 72 hr in the presence of 0.1–2 μM minoxidil analogs dissolved in 0.12N HCl; the final concentration of HCl was 0.0012N or 0.0024N. Cells treated with HCl only served as control. During the last 3 hr of incubation, cells received 100 ascorbic acid to ensure complete hydroxylation of the polypeptide precursors of procollagen (Murad et al, J. Invest. Dermatol. 75:404 (1980)). At the end of the incubation period, cells were harvested by trypsinization and disrupted by sonication in a buffered medium (Murad et al, J. Biol. Chem. 262:11,973 (1987)).

Prolyl and Lysyl Hydroxylase Assays

Lysyl hydroxylase activity in extracts of treated cells was measured with an underhydroxylated procollagen substrate (Murad et al, J. Biol. Chem. 262:11973 (1987)), which was prepared by labeling cultures of human skin fibroblasts with L-[4,5-$^3$H]lysine in the presence of an iron chelator α,α'-dipyridyl (Murad and Pinnell, Conn. Tiss. Res. 13:181 (1985)). The amount of tritium released was quantitated as $^3$H$_O$ after vacuum distillation. Prolyl hydroxylase activity was similarly measured with an underhydroxylated procollagen substrate containing L-[4-$^3$H]proline (Murad and Pinnell, J. Biol. Chem. 262:11973 (1987); Murad and Pinnell, Conn. Tiss. Res. 13:181 (1985)). The enzyme activities are based on a unit of soluble cell protein. The protein content of cell extracts was determined by a dye-binding techniques using Bio-Rad reagents (Bradford, Anal. Biochem. 72:248 (1976)).

Results

Figure 4:
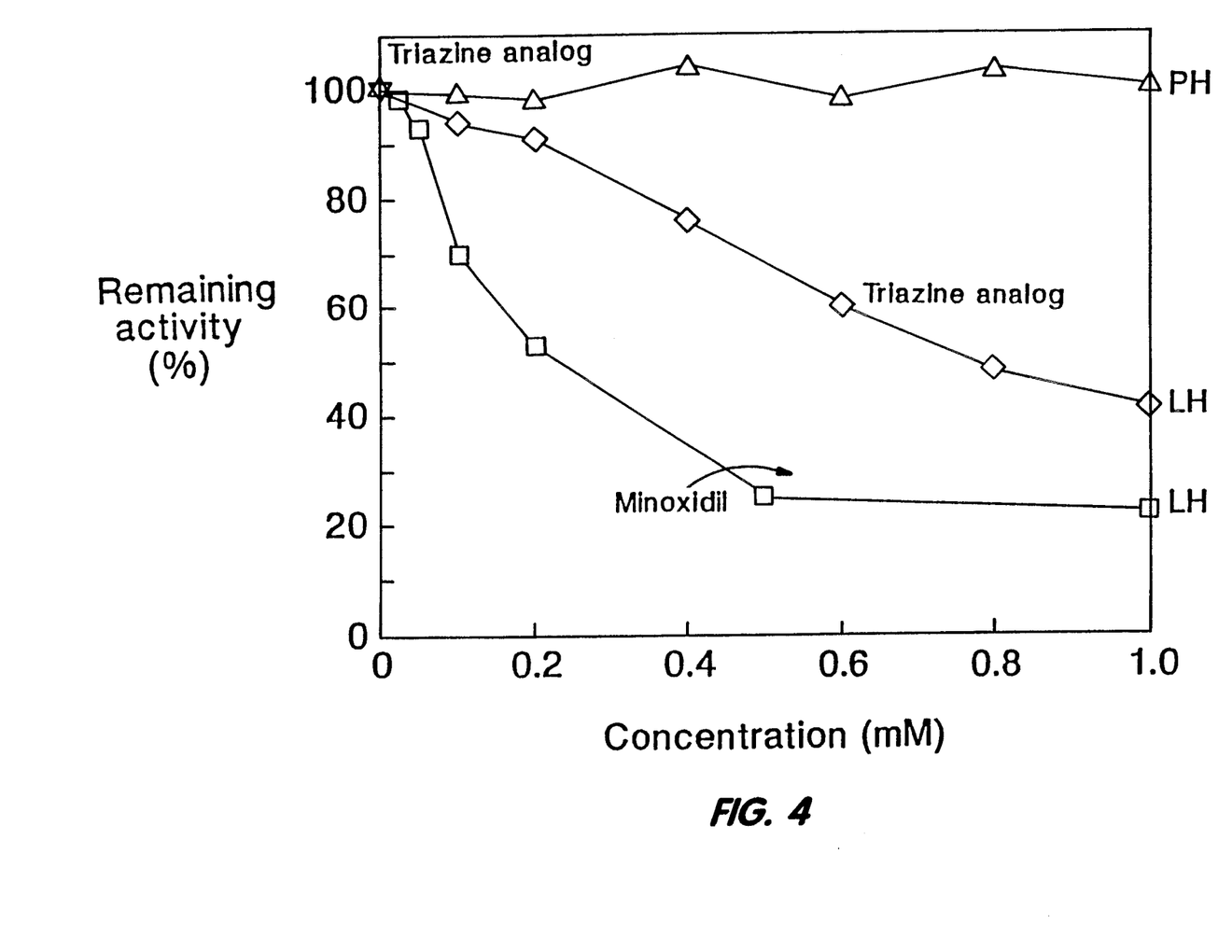
FIG. 4 shows the dose response of changes in prolyl and lysyl hydroxylase activities of fibroblasts treated with minoxidil or its triazine analog. Cells were treated for 72 hr with minoxidil or its triazine analog at the indicated concentrations. The enzyme activities in extracts of treated cells were measured by tritium release assays (Murad and Pinnell, J. Biol. Chem. 262:11,973 (1987)) and are expressed as a percentage of zero-concentration values. PH, prolyl hydroxylase; LH, lysyl hydroxylase.

Results of tests of the inhibitory activity of minoxidil analogs with modified pyrimidine and piperidine rings, are summarized in Table I. Minoxidil analogs in which the pyrimidine ring was replaced with a pyridine ring (compound I) or a symtriazine ring (compound II) decreased the activity of lysyl hydroxylase by 75% and 59% respectively, under conditions where minoxidil decreased it by 73%. The dose response of enzyme inhibition by the triazine analog showed no significant effect up to 0.2 mM, a concentration at which minoxidil gave 50% inhibition (FIG. 4). Higher concentrations of this analog resulted in enzyme inhibition reaching 50% at approximately 0.8 mM. Although less potent than minoxidil, the triazine analog retained specificity for suppression of lysyl hydroxylase activity as indicated from its failure to decrease the activity of prolyl hydroxylase (FIG. 4).

Surprisingly, a structural analog of minoxidil in which the piperidine ring was replaced with an N,N-diethyl group (compound III) was also found to suppress lysyl hydroxylase activity, but those containing an N-ethyl group (compound IV) or an N-butyl group (compound V) were inactive (Table III).

TABLE III

Effect of Minoxidil and Its Structural Analogs on Lysyl Hydroxylase Activity in Cultured Fibroblasts Cells were treated for 72 hr with 1 mM minoxidil or its structural analogs as indicated. The enzyme activity in extracts of treated cells was measured by a tritium-release assay and is expressed as a percentage of HCl-treated control.

| Compound | Pyrimidine Ring Replaced with | Piperdine Ring Replaced with | Lysyl Hydroxylase Activity (%) |
|---|---|---|---|
| Minoxidil | — | — | 27 |
| I | Pyridine | — | 25 |
| II | 1,3,5-Triazine | — | 41 |
| III | — | N,N-Diethyl | 49 |
| IV | — | N-Ethyl | 107 |
| V | — | N-Butyl | 100 |

Figure 5:
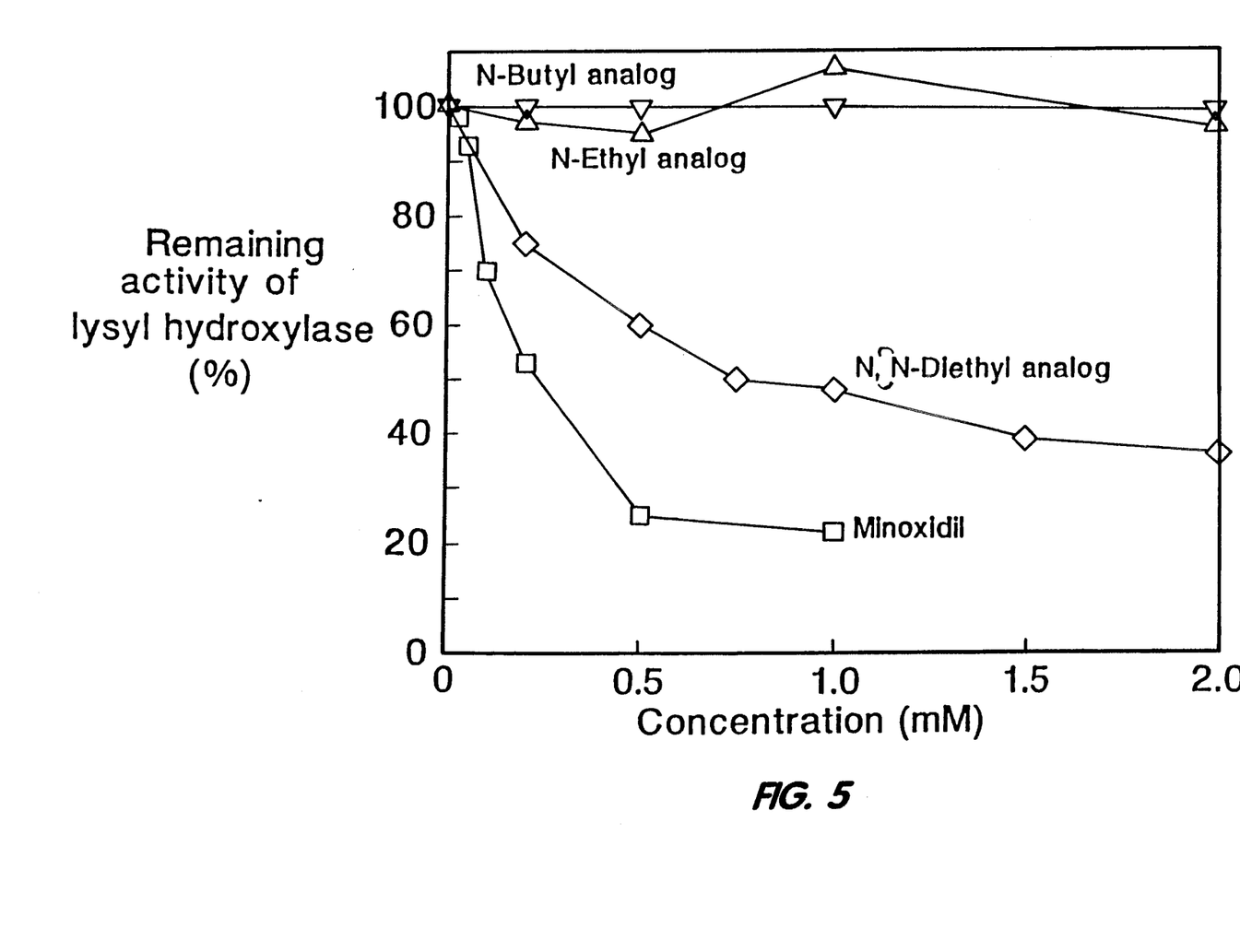
FIG. 5 shows the dose response of changes in lysyl hydroxylase activity of fibroblasts treated with minoxidil or its N-alkyl analogs. Cells were treated for 72 hr with various concentrations of minoxidil or its N-alkyl analogs as indicated. The enzyme activity in extracts of treated cells was measured by tritium release assays (Murad and Pinnell, J. Biol. Chem. 262:11,973 (1987)) and is expressed as a percentage of zero-concentration value. The minoxidil curve is reproduced from FIG. 4.

A comparison of these analogs at various concentrations is presented in FIG. 5, from which it can be calculated that 50% inhibition by the N,N-diethyl analog occurred at approximately 1 mM. Up to 2 mM this analog had no significant effect on prolyl hydroxylase activity. The ability of N,N-diethyl group to replace the piperidine ring of minoxidil in suppressing lysyl hydroxylase activity indicates a requirement for an organic moiety containing a tertiary nitrogen para to the nitroxide oxygen, hence the observed inactivity of N-monoalkyl (ethyl or butyl) analogs.

EXAMPLE 3

Effect of Minoxidil and Its Hydroxy Derivatives on Lysyl Hydroxylation, Lysyl Hydroxylase, and Collagen Synthesis

Fibroblast culture and treatment

Culture of human skin fibroblasts derived from an apparently normal adult were grown to confluent densities in Dulbecco's modified Eagle's medium supplemented with 10% (v/v) fetal calf serum. Thereafter, the medium was replaced with medium supplemented with 0.5% dialyzed fetal calf serum. The cultures were treated for 72 hr with 1 mM minoxidil, 3'- hydroxyminoxidil, or 4'-hydroxyminoxidil (Upjohn) dissolved in aqueous medium. In some experiments, minoxodil was dissolved in 95% (v/v) ethanol; the final concentration of minoxidil was 0.3 mM and that of ethanol was 0.3%. Cultures treated with ethanol only served as the control.

Hydroxylation of proline and lysine residues

During the last 6 hr of treatment, cultures were labeled with 50 $\mu$Ci of L-[2,3-$^3$H]proline (35 Ci/mmol) and 50 $\mu$Ci of L[U-$^{14}$C]lysine (>355 Ci/mmol) in 4 ml of lysine-free medium supplemented with 100 $\mu$M ascorbic acid. At the end of the incubation period, the medium was removed and mixed with 1 mM each of EDTA, N-ethylmaleimide, and phenylmethylsulfonylfluoride, and the collagenous proteins were precipitated with 30% $(NH_4)_2SO_4$. The cell layer was scraped and extracted with 0.5 M acetic acid containing the protease inhibitors as above. The cell extract was neutralized, and the collagenous proteins were precipitated as above. The $(NH_4)_2SO_4$ precipitate from the medium and cell layer was separately dissolved in 0.1% SDS/10 mM Tris-HCl (pH 6.8), reduced with dithiothreitol, and analyzed by electrophoresis on 4% SDS-polyacrylamide gels. The bands corresponding to the proa1(I) and proa2(I) chains from the two fractions were pooled and hydrolyzed with 6 M HCl for 24 hr at 110° C. Proline, hydroxyproline, lysine, and hydroxylysine in the hydrolysate were separated by HPLC (Takimitsa et al, J. Dermatol. 16:37 (1989)), and their radioactivity was determined in a Beckman liquid scintillation counter. To isolate type I procollagen the precipitate from the medium and cell layer was separately dissolved in 25 mM Tris-HCl, pH 7.5, containing 2 M urea and 1 mM each of EDTA, N-ethylmaleimide, and phenylmethylsulfonylfluoride, then chromatographed on a DEAE-cellulose column (Freiberger et al, J. Invest. Dermatol. 75:425 (1980)). The procollagen isolated from the two fractions was pooled, hydrolyzed, and analyzed as above.

Prolyl and lysyl hydroxylase assays

During the last 3 hr of treatment, cultures received 100 $\mu$M ascorbic acid. The enzyme activities in extracts of treated cells were measured by tritium-release assays described previously (Murad and Pinnell, J. Biol. Chem. 262:11,973 (1987)).

Collagen synthesis

During the last 6 hr of treatment, cultures were labeled with 20 $\mu$Ci of L-[2,3-$^3$H]proline in 1 ml of medium supplemented with 100 $\mu$M ascorbic acid. The amount of proline radioactivity incorporated into collagen in the medium and cells combined was measured after digestion with a bacterial collagenase, essentially as described previously (Freiberger et al, J. Invest. Dermatol. 75:425 (1980)).

Results

The extent of hydroxylation of labeled proline and lysine in type I procollagen synthesized by fibroblasts treated with minoxidil was determined. In these cells, the ratio of hydroxylysine to lysine in the procollagen isolated by gel chromatography was 27% of control value and that in the procollagen isolated by column chromatography was 50% of control; the ratio of hydroxypyroline to proline remained unaltered (Table IV).

TABLE IV

Effect of Minoxidil on Prolyl and Lysyl Hydroxylations in Human Skin Fibroblasts

| Treatment[a] | Hyp/Pro | Hyl/Lys |
| --- | --- | --- |
| Control | 0.92 ± .01[b] | 0.30 ± 0.05[b] |
| Minoxidil, 0.3 M | 0.91 ± .03[b] | 0.08 ± 0.02[b] |
| Control | 0.84[c] | 0.34[c] |
| Minoxidil, 0.3 M | 0.81[c] | 0.17[c] |

[a]72 hr.
[b]Mean ± range of values from two separate experiments; the values are for type I procollagen chains isolated by gel electrophoresis.
[c]The values are for type I procollagen isolated by column chromatography.

The two methods of purification gave comparable values for lysyl hydroxylation in control fibroblasts, and these values are similar to those reported earlier (Tajima et al, Collagen Rel. Res. 3:511 (1983)).

A comparison of the effects of minoxidil and its hydroxy derivatives on the extent of hydroxylation of proline and lysine in the procollagen isolated by gel chromatography is shown in Table V.

TABLE V

Effect of Minoxidil and its Hydroxy Derivatives on Prolyl and Lysyl Hydroxylations in Human Skin Fibroblasts

| Treatment[a] | Hyp/Pro | Hyl/Lys |
| --- | --- | --- |
| Control | 0.92 ± .00 | 0.22 ± 0.03 |
| Minoxidil, 1 mM | 0.92 ± .01 | 0.07 ± 0.02 |
| 3'-Hydroxyminoxidil, 1 mM | 0.95 ± 0.02 | 0.07 ± 0.01 |
| 4'-Hydroxyminoxidil, 1 mM | 1.12 ± 0.07 | 0.09 ± 0.01 |

[a]72 hr.
[b]Mean ± range of values from two separate experiments; the values are for type I procollagen chains isolated by gel electrophoresis.

Expressed as the percentage of control value, the ratio of hydroxylysine to lysine in the procollagen synthesized by minoxidil-treated fibroblasts was 32% and that in the procollagen synthesized by fibroblasts treated with 3'-hydroxyminoxidil or 4'-hydroxyminoxidil was 32% and 41%, respectively. The ratio of hydroxyproline to proline under these conditions was 100%, 103%, and 122% control value, respectively.

Fibroblasts treated with minoxidil, 3'-hydroxyminoxidil, or 4'-hydroxyminoxidil were also analyzed for prolyl and lysyl hydroxylase activities, and the data are presented in Table VI.

TABLE VI

Effect of Minoxidil and its Hydroxy Derivatives on Prolyl and Lysyl Hydroxylase Levels in Human Skin Fibroblasts

| Treatment[a] | Prolyl Hydroxylase Activity | Lysyl Hydroxylase Activity |
| --- | --- | --- |
| | cpm $^3$H$_2$O/mg protein | |
| Control | 26762 | 1211 |
| Minoxidil, 1 mM | 29446 | 308 |

TABLE VI-continued

Effect of Minoxidil and its Hydroxy Derivatives
on Prolyl and Lysyl Hydroxylase Levels
in Human Skin Fibroblasts

| Treatment[a] | Prolyl Hydroxylase Activity | Lysyl Hydroxylase Activity |
|---|---|---|
| 3'-Hydroxyminoxidil, 1 mM | 30512 | 263 |
| 4'-Hydroxyminoxidil, 1 mM | 33500 | 239 |

[a] 72 hr.

Lysyl hydroxylase activity in extracts of these cells was 25%, 22%, and 20 of control level, respectively, whereas prolyl hydroxylase activity remained unchanged.

The synthesis of collagen relative to that of total protein was reduced by 25% in fibroblasts treated with minoxidil compared with control (Table VII).

TABLE VII

Effect of Minoxidil and its Hydroxy Derivatives
on Collagen Synthesis in Human Skin Fibroblasts

| Treatment[a] | % Collagen Synthesized[b] |
|---|---|
| Control | 8.8 ± 0.1 |
| Minoxidil, 1 mM | 6.6 ± 0.7 |
| 3'-Hydroxyminoxidil, 1 mM | 9.0 ± 0.9 |
| 4'-Hydroxyminoxidil, 1 mM | 8.2 ± 0.6 |

[a] 72 hr.
[b] Mean ± SD of values from duplicate analysis of two cultures.

This effect appears to be unrelated to the observed inhibition of lysyl hydroxylation since collagen synthesis remained unchanged in fibroblasts exposed to the hydroxy derivatives of minoxidil despite similarly diminished hydroxylation (Table V).

EXAMPLE 4

Effect of Minoxidil and Its Hydroxy Derivatives on Cell Proliferation

Figure 6:
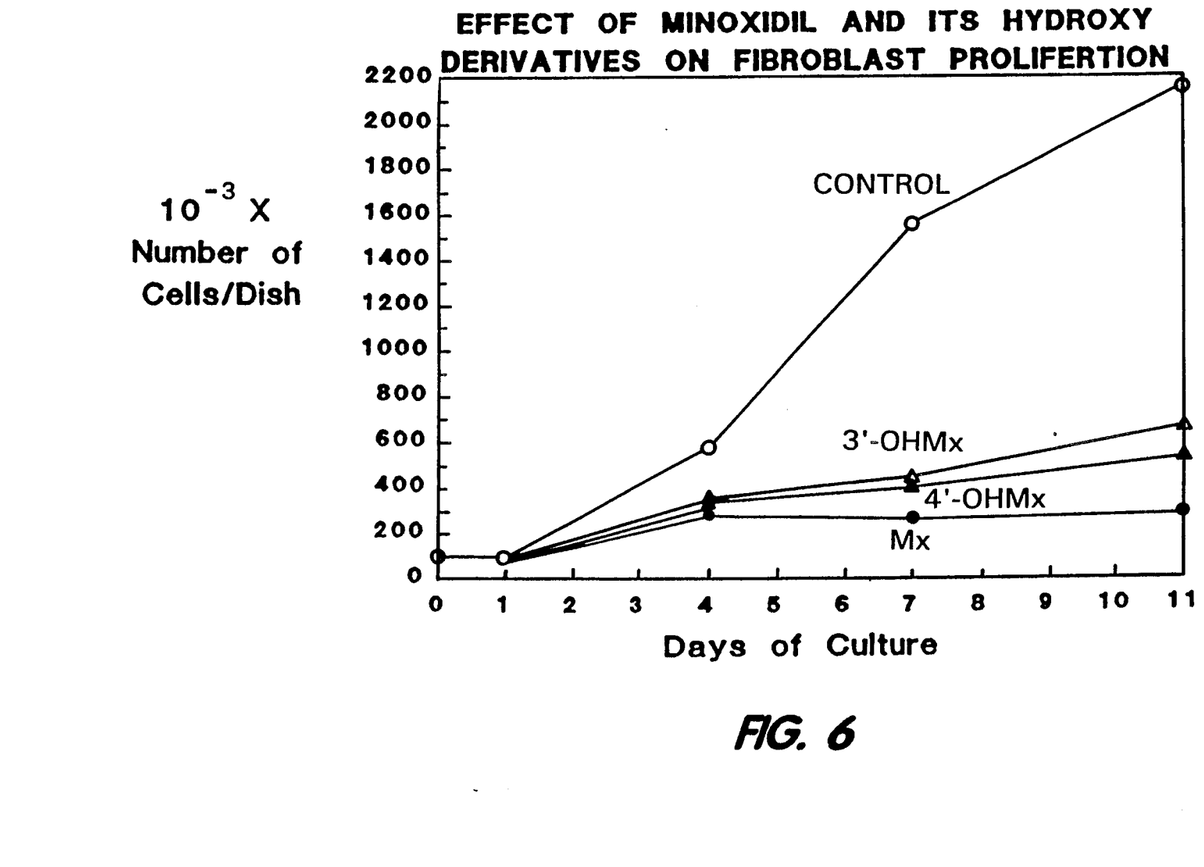
FIG. 6 shows the effect of minoxidil and its hydroxy derivatives on fibroblast proliferation.

FIG. 6 shows the results of studies run in order to determine the effect of minoxidil and its 3'-and 4'-hydroxy derivatives on proliferation of human skin fibroblasts in culture. Cultures were seeded at a density of 100,000 cells per 35 mm-dish and allowed to attach and proliferate in the presence of 20% calf serum. Drug-treated cultures received 1 mM minoxidil or its hydroxy derivative on day 1 after seeding.

EXAMPLE 5

Figure 7:
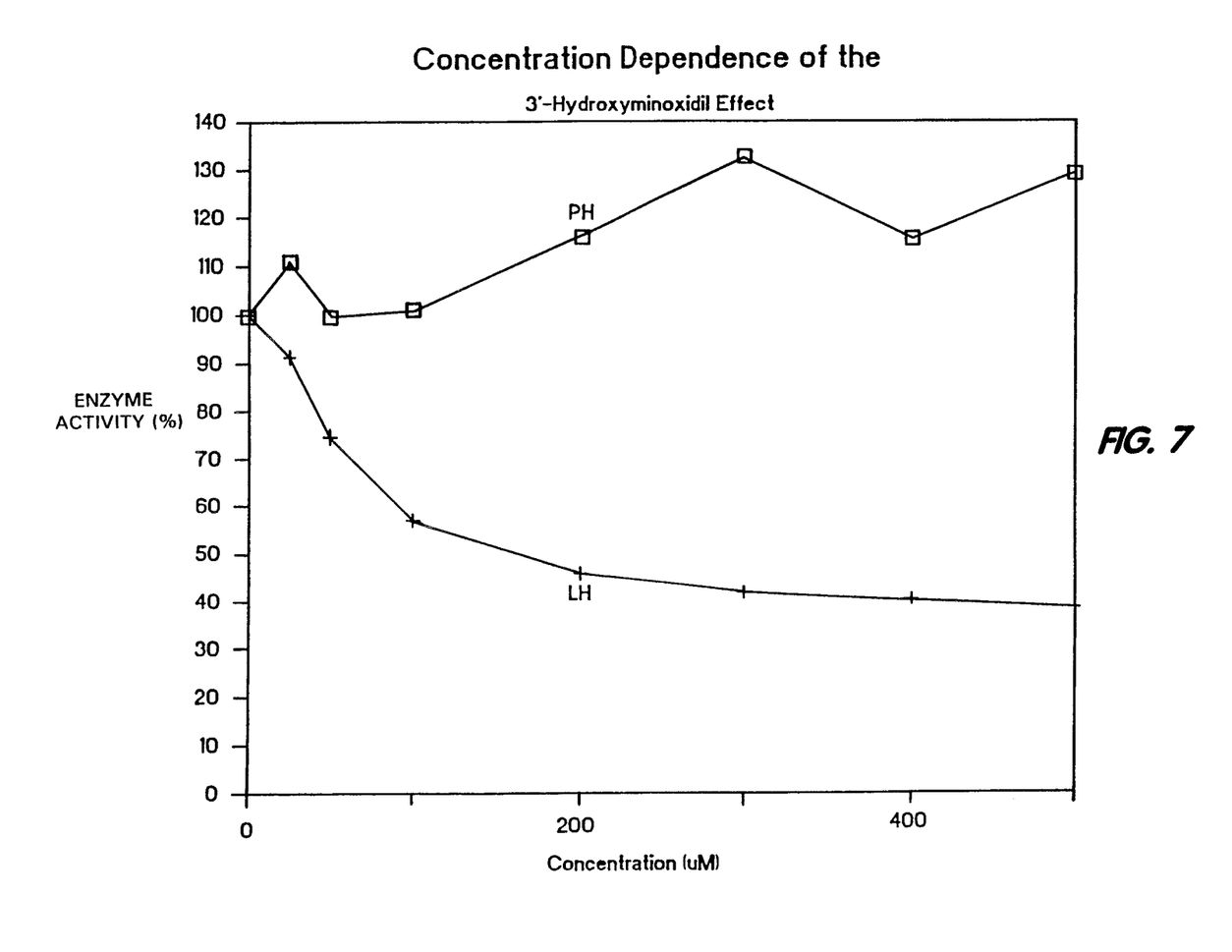
FIG. 7 shows the concentration dependence of the effect of 3'-hydroxyminoxidil.
Figure 8:
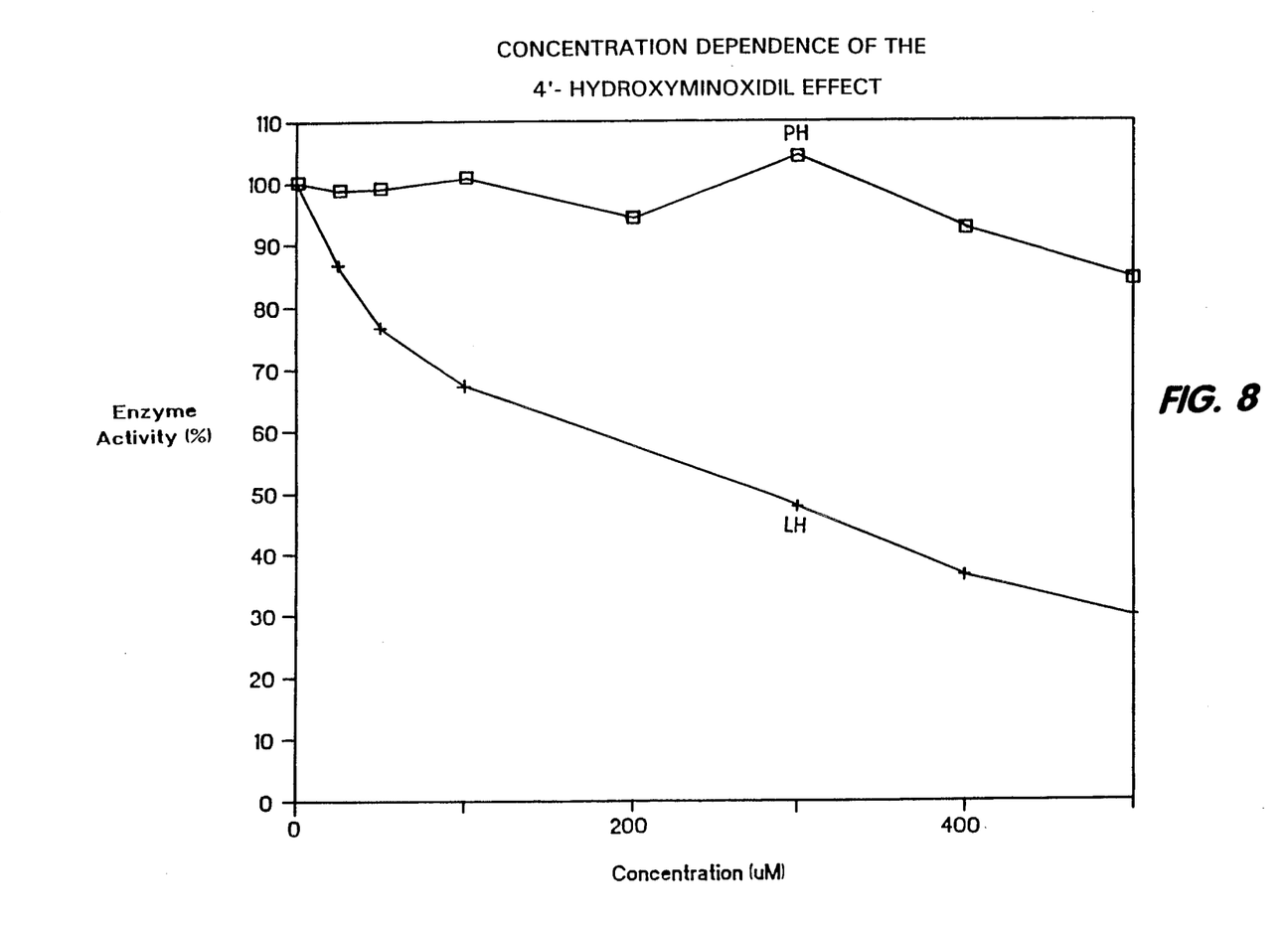
FIG. 8 shows the concentration dependence of the effect of 4'-hydroxyminoxidil.

FIGS. 7 and 8 show the concentration dependence of the effect of 3'-hydroxy and 4'-hydroxy derivatives of minoxidil, respectively, on prolyl hydroxylase (PH) and lysyl hydroxylase (LH) levels in human skin fibroblasts.

All documents cited above are incorporated herein, in their entirety, by reference.

One skilled in the art will appreciate from a reading of the foregoing that various changes in form and detail can be made without departing from the true scope of the invention.

What is claimed is:

1. A method of treating a fibrotic condition comprising administering to a patient suffering from said condition an amount of a minoxidil derivative bearing a hydroxy group on the piperidino moiety thereof sufficient to effect said treatment.

2. The method of claim 1 wherein said hydroxy group is at the 3 position.

3. The method of claim 1 wherein said hydroxy group is at the 4 position.

4. The method of claim 1 wherein said condition is scleroderma.

5. The method of claim 1 wherein said condition is cirrhosis.

6. The method of claim 1 wherein said condition is fibrosis.

7. The method of claim 1 wherein said condition is keloids.

8. A method of treating abnormal wound healing comprising administering to a patient in need of such treatment an amount of a minoxidil derivative bearing a hydroxy group on the piperidino moiety thereof sufficient to effect said treatment.

9. The method of claim 8 wherein the hydroxy group is at the 3 position.

10. The method of claim 8 wherein the hydroxy group is at the 4 position.

11. A method of controlling excessive collagen crosslink formation comprising administering to a patient suffering from a condition resulting from excessive collagen crosslink formation an amount of a minoxidil derivative bearing a hydroxy group on the piperidino moiety thereof sufficient to effect said control.

12. The method of claim 11 wherein said hydroxy group is at the 3 position.

13. The method of claim 11 wherein said hydroxy group is at the 4 position.

* * * * *